United States Patent
Friebe et al.

(10) Patent No.: US 6,887,864 B2
(45) Date of Patent: May 3, 2005

(54) AZEPANE DERIVATIVES

(75) Inventors: Walter-Gunar Friebe, Mannheim (DE); Birgit Masjost, Munich (DE); Ralf Schumacher, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/383,111

(22) Filed: Mar. 6, 2003

(65) Prior Publication Data

US 2003/0181716 A1 Sep. 25, 2003

(30) Foreign Application Priority Data

Mar. 12, 2002 (EP) .............................. 02005287
Mar. 26, 2002 (EP) .............................. 02006648

(51) Int. Cl.[7] ............... C07D 401/00; C07D 405/00; C07D 409/00; C07D 403/00; A61K 31/55
(52) U.S. Cl. ................ 514/217.03; 514/217.04; 514/217.05; 514/217.06; 514/217.07; 514/217.08; 514/217.09; 514/217.1; 514/217.11; 540/596; 540/597; 540/598; 540/599; 540/600; 540/601; 540/602; 540/603; 540/604; 540/605; 540/606; 540/607; 540/608
(58) Field of Search ................ 540/596, 597, 540/598, 599, 600, 601, 602, 603, 604, 605, 606, 607, 608; 514/217.03, 217.04, 217.05, 217.06, 217.07, 217.08, 217.09, 217.1, 217.11

(56) References Cited

FOREIGN PATENT DOCUMENTS

| EP | 296 110 | 12/1988 |
|----|---------|---------|
| EP | 657 458 | 6/1995 |
| EP | 663 393 | 7/1995 |
| EP | 802 190 | 10/1997 |
| EP | 1 020 471 | 7/2000 |
| WO | WO 94/20062 | 9/1994 |
| WO | WO 95/30640 | 11/1995 |
| WO | WO 97/02249 | 1/1997 |

OTHER PUBLICATIONS

David Tanner, et al., Tetrahedron, vol. 53, No. 13, pp. 4857–4868 (1997).

G. Erik Jagdmann, Jr., et al., Bioorganic & Medicinal Chemistry Letters, vol. 5, No. 17, pp. 2015–2020 (1995).

*Primary Examiner*—Bruck Kifle
(74) *Attorney, Agent, or Firm*—George W. Johnston; Patricia S. Rocha-Tramaloni

(57) ABSTRACT

This invention provides novel azepane derivatives or pharmaceutically acceptable salts thereof, according to the general formula (I)

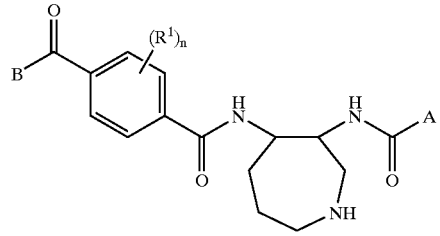

wherein the symbols are defined in the specification, as well as processes for their manufacture. The compounds according to this invention possess anti-cell proliferation activity and show an increased plasma-stability.

15 Claims, No Drawings

AZEPANE DERIVATIVES

FIELD OF THE INVENTION

The invention relates to novel azepane derivatives, or pharmaceutically acceptable salts thereof, which possess anti-cell-proliferation activity such as anti-cancer activity and are accordingly useful in treating human or other animal body. The invention also relates to processes for the manufacture of the azepane derivatives, to pharmaceutical compositions containing them and to the manufacture of pharmaceutical compositions in the production of an anti-cell-proliferation effect in a warm-blooded animal such as man.

BACKGROUND OF THE INVENTION

Cell signaling pathways regulate cell growth, proliferation, and apoptosis. Kinases transduct signals for cell growth or apoptosis by phosphorylation of their substrates, which are mostly downstream kinases involved in cell signaling processes themselves. The activity of kinases is regulated by phosphorylation and dephosphorylation effecting conformational changes in the kinases. Overexpression or constitutive activation of kinases involved in anti-apoptotic or proliferation signaling pathways are one typical feature of tumor cells (Cross, T. G., et al., Exp. Cell Res. 256 (2000) 34–41).

The family of serine/threonine kinases (AKT) proteins are located downstream in the PI-3 kinase pathway and phosphorylate a burgeoning list of substrates involved in several pathways for cell survival and inhibition of apoptosis as has been shown recently (Kandel, E. S., and Hay, N., Exp. Cell Res. 253 (1999) 210–229; Blume-Jensen, P., and Hunter, T., Nature 411 (2001) 355–365; Datta, S. R., et al., Genes Dev. 13 (1999) 2905–2927). Constitutive activation of AKT1 is frequently found in human prostate, breast, and ovarian carcinomas. It is due to a complete loss of lipid phosphatase PTEN gene, a negative regulator of the PI-3 kinase pathway (Nesterov, A., et al., J. Biol. Chem. 276 (2001) 10767–10774). These data indicate that AKT1 kinase is a central player in tumorigenesis and a potential target for cancer intervention. Inhibitors of AKT1 kinase are promising reagents for cancer therapy as effective sensitizers or inducers of apoptosis (Beresford, S. A., et al., J. Interferon Cytokine Res. 21 (2001) 313–322).

AKT1 belongs to the family of protein kinases. It exhibits a sequence homology to PKC and PKA. Several structural classes of PKC and PKA inhibitors are known. More specifically, WO 94/20062 (by Sphinx Pharmaceuticals Corporation, "Balanoids"), WO 95/30640 (by Eli Lilly and company, "Substituted fused and bridged bicyclic compounds as therapeutic agents"), WO 97/02249 (by F. Hoffmann-La Roche, "Novel azepanes and their ring homologues for therapy and prophylaxis of protein kinase mediated diseases"), and EP 0 663 393-A1 (by F. Hoffmann-La Roche, "Neue 3-Amino/Hydroxy-4-[4-Benzoyl-Phenyl Carbonylamino/oxy]-Azepane und Homologe als Protein Kinase Hemmer") disclose balanol derivatives with PKC inhibitory activity. Bisindolylmaleimides are reported as PKC inhibitors in EP 0 657 458-A1 (by Eli Lilly, "Protein kinase C inhibitors"), EP 1 020 471-A1 (by Kyowa Hakko Kogyo Co., "Process for producing UCN-01"), and EP 0 296 110-A2 (by Ciba-Geigy AG, "An Methylamino-Stickstoff substituierte Derivate von Staurosporin"). No AKT1 small molecule inhibitors are disclosed in the literature.

It has now been found that certain novel azepane derivatives are potent inhibitors of AKT1 in vitro and in various tumor cell lines, possess anti-cell-proliferation properties, induce apoptosis and are plasma stable which makes them more potent than those in the aforementioned references.

SUMMARY OF THE INVENTION

According to the invention, there is provided a novel azepane derivative of the formula I

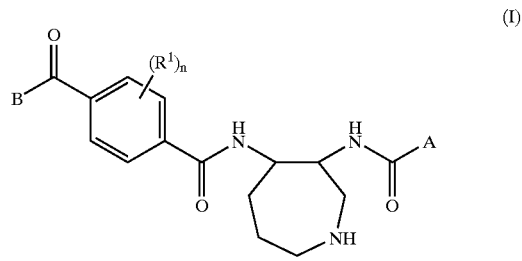

wherein
A denotes
  a carbocyclic group; or a
  a heterocyclic group;
n is 0–4;
each $R^1$ is the same or different residue, independently selected from a halogen atom, a (1–4C)alkyl-, or a (1–4C) alkoxy-group;
B denotes
  a phenyl ring which may be unsubstituted or substituted by 1, 2, or 3 substituents independently selected from a halogen atom, an (1–4C)alkyl, trifluoromethyl, hydroxy, (1–4C)alkoxy, nitro, amino, amino(1–4C) alkyl, (1–4C)alkylamino, di[(1–4C)alkyl]amino, (1–4C)alkanoylamino, (1–4C)alkylthio, (1–4C) alkoxycarbonyl, a (1–3C)alkylenedioxy, an acyl, a carbocyclic or a heterocyclic group, and which may be annulated by a carbocyclic group or by a heterocyclic group, or
  a heterocyclic group, its stereoisomers, enantiomers and racemates, or a pharmaceutically acceptable salt thereof A carbocyclic group may be
a non-aromatic, preferably mono- or bicyclic ring system with 3–7 carbon atoms, for example, cyclopentane, cyclohexane, cyclohexene or cyclopropane, which may be unsubstituted or substituted by 1, 2, or 3 substituents independently selected from a halogen atom, an (1–4C) alkyl, trifluoromethyl, hydroxy, (1–4C)alkoxy, aryl, hetaryl, arylalkyl, arylalkyloxy, aryloxy, (1–3C) alkylenedioxy, nitro, amino, (1–4C)alkylamino, di[(1–4C)alkyl]amino, (1–4C)alkanoylamino or an acyl group, and which may be annulated by an aryl or hetaryl group, to form, for example, an indane or a tetraline, or an aryl group.

An aryl group is a carbocyclic, preferably mono- or bicyclic, conjugated ring system, for example, phenyl, naphthyl, preferably phenyl, which may be unsubstituted or substituted by 1, 2, or 3 substituents independently selected from a halogen atom, an (1–4C)alkyl, trifluoromethyl, hydroxy, (1–4C)alkoxy, arylalkyloxy, aryloxy, (1–3C) alkylenedioxy, nitro, amino, (1–4C)alkylamino, di[(1–4C) alkyl]amino, (1–4C)alkanoylamino, or an acyl group.

A heterocyclic group may be
a non-aromatic, preferably mono- or bicyclic ring system with 3–7 members and one or two hetero atoms independently chosen from nitrogen, oxygen, and sulfur, for example, piperidino, morpholino, pyrrolidino, piperazino, which may be unsubstituted or substituted by 1, 2, or 3 substituents independently selected from a halogen atom, an (1–4C)alkyl, trifluoromethyl, hydroxy, (1–4C)alkoxy, aryl, hetaryl, arylalkyl, arylalkyloxy, aryloxy, (1–3C) alkylenedioxy, nitro, amino, (1–4C)alkylamino, di[(1–4C)alkyl]amino, (1–4C)alkanoylamino, or an acyl group, and which maybe annulated by an aryl or hetaryl group, to form, for example, a tetrahydroquinoline, tetrahydroisoquinoline or a dihydroindole; or a hetaryl group.

A hetaryl group may be either a 5 or 6 membered cyclic conjugated ring system with one or two hetero atoms independently chosen from nitrogen, oxygen, and sulfur, for example, pyridinyl, pyrimidinyl, thiophenyl, furyl or pyrrolyl, or an annulated bicyclic conjugated ring system like indolyl, quinolyl or isoquinolyl, which may be unsubstituted or substituted by 1, 2, or 3 substituents independently selected from a halogen atom, an (1–4C)alkyl, trifluoromethyl, hydroxy, (1–4C)alkoxy, arylalkyloxy, aryloxy, (1–3C)alkylenedioxy, nitro, amino, (1–4C) alkylamino, di[(1–4C)alkyl]amino, (1–4C)alkanoylamino, or an acyl group.

A preferred value for a substituent when it is a halogen atom is, for example, fluoro, chloro, bromo and iodo; when it is (1–4C)alkyl is, for example, methyl, ethyl, propyl, isopropyl, n-butyl, isobutyl, sec-butyl, tert-butyl; when it is (1–4C)alkoxy is, for example, methoxy, ethoxy, propoxy, isopropoxy or butoxy; when it is amino(1–4C)alkyl is, for example, aminomethyl, 1- or 2-aminoethyl or 1-, 2- or 3-aminopropyl; when it is (1–4C)alkylamino is, for example, methylamino, ethylamino or propylamino; when it is di-[(1–4C)alkyl]amino is, for example, dimethylamino, N-ethyl-N-methylamino, diethylamino, N-methyl-N-propylamino or dipropylamino; when it is (1–4C) alkanoylamino is, for example, formylamido, acetamido, propionamido or butyramido; when it is (1–3C) alkylenedioxy is, for example, methylenedioxy, ethylenedioxy or propylenedioxy; and when it is acyl is, for example, formyl, acetyl, propionyl, benzoyl, or phenylacetyl.

Enantiomers, diastereoisomers, racemates and mixtures thereof and pharmaceutically acceptable salts of azepane derivatives of the formula I are also part of the invention.

"Pharmaceutically acceptable salt" refers to conventional acid-addition salts or base-addition salts that retain the biological effectiveness and properties of the compounds of formula I and are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as, for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

A preferred embodiment of the invention are the compounds of formula (I), wherein A is a carbocyclic or heterocyclic group;

B is a phenyl ring which may be unsubstituted or substituted by 1, 2 or 3 substituents independently selected from a halogen atom, an (1–4C)alkyl, trifluoromethyl, hydroxy, (1–4C)alkoxy, nitro, amino, (1–4C)alkylamino, di[(1–4C) alkyl]amino, (1–4C)alkanoylamino, (1–4C)alkylthio, (1–4C)alkoxycarbonyl, a (1–3C)alkylenedioxy, an acyl, a carbocyclic or a heterocyclic group, and which may be annulated by a carbocyclic group or by a heterocyclic group, or a heterocyclic group;

$(R^1)_n$ is the same or different halogen atom, a (1–4C) alkyl-, or a (1–4C)alkoxy-group, and n=0–4;

its stereoisomers, enantiomers or racemates, or a pharmaceutically aceptable salt thereof.

Another preferred embodiment of the invention are the compounds of formula (I), wherein A is pyridine, 2-aminopyridine or pyrimidine;

B is a substituent, chosen from 2-fluoro-6-hydroxy-3-methoxy-phenyl, 2-fluoro-6-hydroxy-3-methyl-phenyl, 6-hydroxy-3-methylsulfanyl-phenyl, 6-hydroxy-2,3-dihydro-benzo[1,4]dioxine-5-yl, 6-hydroxy-2,3-dimethoxy-phenyl, 2-hydroxy-5-methoxy-phenyl, 2-hydroxy-5-methyl-phenyl, 5-hydroxy-2-methyl-pyridine-4-yl, 3-fluoro-5-hydroxy-2-methyl-pyridine-4-yl, 8-fluoro-6-hydroxy-quinoline-7-yl, 8-fluoro-6-hydroxy-2-methyl-quinoline-7-yl, 2-tert-butyl-8-fluoro-6-hydroxy-quinoline-7-yl, 6-hydroxy-quinoline-5-yl, 3-dimethylamino-2-fluoro-6-hydroxy-phenyl, 5-dimethylamino-2-hydroxy-phenyl, 2-hydroxy-5-piperidin-1-yl-phenyl, 2-fluoro-6-hydroxy-3-piperidin-1-yl-phenyl, 3-(3,3-dimethyl-piperidin-2-yl)-2-fluoro-6-hydroxy-phenyl, 3-(3,3-dimethyl-piperidin-2-yl)-6-hydroxy-phenyl;

$(R^1)_n$ is the same or different halogen atom, a (1–4C) alkyl-, or a (1–4C)alkoxy-group;

and n=0.

According to a further aspect of the invention, there is provided a pharmaceutical composition which comprises an azepane derivative of the formula I, or a pharmaceutically acceptable salt thereof, as defined hereinabove in association with a pharmaceutically acceptable diluent or carrier. The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general, the above compositions may be prepared in a manner using conventional excipients. The azepane derivative will normally be administered to a warm-blooded animal at a unit dose within the range of about 5 to about 5000 mg per square meter body area of the animal, i.e., from about 0.1 to about 100 mg/kg, and this normally provides a therapeutically effective dose. A unit dose form such as a tablet or capsule will usually contain, for example, from about 1 to about 250 mg of active ingredient. Preferably, a daily dose in the range of about 1 to about 100 mg/kg is employed. However, the daily dose will necessarily be varied depending upon the host treated, the particular route of administration, and the severity of the illness being treated. Accordingly, the optimum dosage may be determined by the practitioner who is treating any particular patient.

According to a further aspect of the present invention, there is provided an azepane derivative of the formula I as defined hereinabove for use in a method of treatment of the human or animal body by therapy. It has now been found that the compounds of the present invention possess anti-cell-proliferation properties which are believed to arise from their AKT1 inhibitory activity. Accordingly, the compounds of the present invention provide a method for treating the proliferation of malignant cells. Further, the compounds of the present invention are expected to be useful in the treatment of cancer by providing an anti-proliferative effect, particularly in the treatment of cancers of the breast, lung, colon, rectum, stomach, prostate, bladder, pancreas and ovary. Additionally, it is expected that a derivative of the present invention will possess activity against a range of leukemias, lymphoid malignancies and solid tumors such as carcinomas and sarcomas in tissues such as the liver, kidney, prostate and pancreas.

Thus, according to this aspect of the invention, there is provided the use of an azepane derivative of the formula I, or a pharmaceutically acceptable salt thereof, as defined herein in the manufacture of a pharmaceutical composition for use in the production of an anti-cell-proliferation effect in a warm-blooded animal such as a human being.

According to a further aspect of the invention, there is provided a method for producing an anti-cell-proliferation effect in a warm-blooded animal, such as man, in need of such treatment which comprises administering to the animal an effective amount of an azepane derivative as defined hereinabove.

The anti-cell-proliferation treatment defined hereinabove may be applied as a sole therapy or may involve, in addition to the azepane derivative of the invention, one or more other anti-tumor substances, for example, those selected from, mitotic inhibitors, such as vinblastine; alkylating agents, such as cis-platin, carboplatin and cyclophosphamide; inhibitors of microtubule assembly, like paclitaxel or other taxanes; antimetabolites, such as 5-fluorouracil, capecitabine, cytosine arabinoside and hydroxyurea, or intercalating antibiotics, such as adriamycin and bleomycin; immunostimulants, such as trastuzumab; DNA synthesis inhibitors, such as gemcitabine; enzymes, such as asparaginase; topoisomerase inhibitors, such as etoposide; biological response modifiers, such as interferon; and anti-hormones, such as antiestrogens like tamoxifen or, antiandrogens like (4'-cyano-3-(4-fluorophenylsulphonyl)-2-hydroxy-2-methyl-3'-(trifluoromethyl)propionanilide, or other therapeutic agents and principles as described in, for example, Cancer: Principles & Practice of Oncology, Vincent T. DeVita, Jr., Samuel Hellmann, Steven A. Rosenberg; 5th ed., Lippincott-Raven Publishers, 1997. Such conjoint treatment may be achieved by way of the simultaneous, sequential or separate dosing of individual components of the treatment. According to this aspect of the invention, there is provided a pharmaceutical product comprising an azepane derivative of the formula I as defined hereinabove and an additional anti-tumor substance as defined hereinabove for the conjoint treatment of cancer.

Another aspect of the present invention are pharmaceutical compositions containing a pharmacologically effective amount of one or more compounds of formula I in admixture with a pharmaceutically acceptable excipient and/or diluent.

Examples of physiologically acceptable salts of compounds of formula I are salts with physiologically acceptable acids. These salts can be, among others, hydrochloride, sulfate, mesylate, succinate, tartrate, acetate, and phosphate.

DETAILED DESCRIPTION OF THE INVENTION

An azepane derivative of formula I, or a pharmaceutically-acceptable salt thereof, may be prepared by any process known to be applicable to the preparation of chemically-related compounds. Such processes, when used to prepare an azepane derivative of the formula I, or a pharmaceutically-acceptable salt thereof, are provided as a further feature of the invention and are illustrated by the following representative examples in which, unless otherwise stated, A, B and $R^1$ have any of the meanings defined hereinabove and $R^2$ is a suitable protecting group, preferably t-butoxycarbonyl or methoxymethyl. Necessary starting materials may be obtained by standard procedures of organic chemistry. The preparation of such starting materials is described within the accompanying non-limiting examples. Alternatively, necessary starting materials are obtainable by analogous procedures to those illustrated which are within the ordinary skill of an organic chemist.

The preferred method for the production of compounds of formula I involves the reaction of compounds of formula II

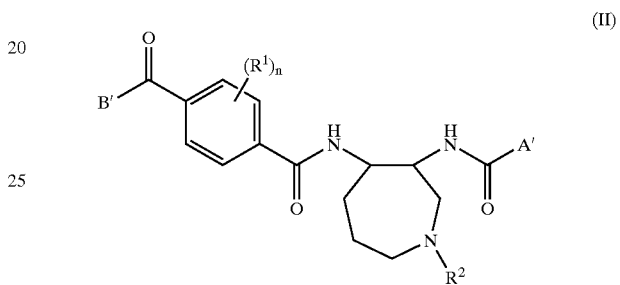

(II)

wherein $R^1$ and $R^2$ are defined hereinabove and A' and B' represent A and B as defined hereinabove, or a suitably protected derivative thereof, with a deprotecting agent, for example HCl in dioxane at room temperature. Suitable protecting groups are for example t-butoxycarbonyl or methoxymethyl.

Compounds of formula II are prepared from compounds of formula III and IV wherein A', B', $R^1$ and $R^2$ are defined hereinabove.

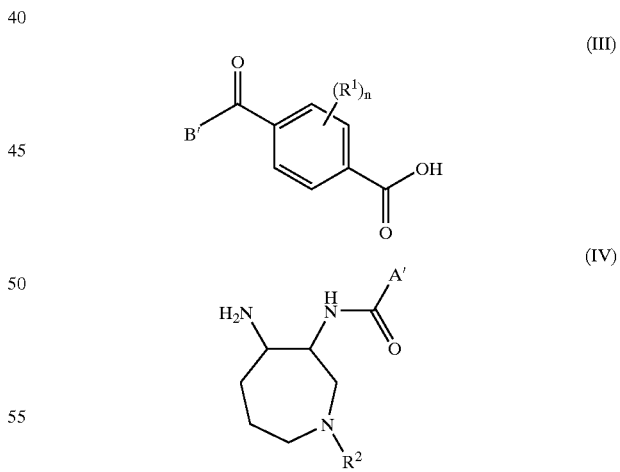

(III)

(IV)

This reaction typically involves a two-step one-pot procedure. In the first step, the carboxylate of the formula III becomes activated. This reaction is carried out in an inert solvent or diluent, for example, in dichloromethane, dioxane, or tetrahydrofuran, in the presence of an activating agent. A suitable reactive derivative of an acid is, for example, 1) the product of the reaction of the acid and a carbodiimide such as dicyclohexylcarbodiimide; 2) the product of the reaction of the acid and bis-(2-oxo-3- oxazolidinyl)-phosphorylchloride; 3) the product of the reaction of the acid and carbonyldiimidazole; 4) the product of the reaction of the acid and N-hydroxysuccinimide; 5) an acyl halide, for example, an acyl chloride formed by the reaction of the acid and an inorganic acid chloride, such as thionyl chloride; 6) a mixed anhydride, such as an anhydride formed by the reaction of the acid and a chloroformate, such as isobutyl chloroformate; 7) an active ester, such as an ester formed by the reaction of the acid and a phenol, such as pentafluorophenol; 8) an active ester formed by the reaction of the acid and N-hydroxybenzotriazole; 9) an acyl azide, such as an azide formed by the reaction of the acid and an azide, such as diphenylphosphoryl azide; and 10) an acyl cyanide, such as a cyanide formed by the reaction of an acid and a cyanide, such as diethylphosphoryl cyanide. The activation reaction is carried out between about −30° C. to about 60° C., conveniently at or below 0° C. In the second step, the amine of the formula IV is added to the solution, at the temperature used for the activation, and the temperature is slowly adjusted to ambient temperature. An appropriate scavenger base, like dimethylaminopyridine, triethylamine, or diisopropylethlylamine may be added to the reaction mixture. These methods are well known to those skilled in the art. In principle, all methods for the synthesis of amides as used in peptide chemistry as described in for example "Methoden der organischen Chemie (Houben-Weyl)" Band XV/1 and XV/2.

Compounds of formula IV may be prepared from compounds of formula V,

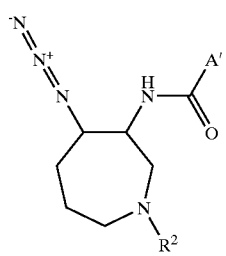

(V)

wherein A' and $R^2$ are defined hereinabove, by reaction of V with hydrogen and, for example, 10% Pd/C in THF and ethanol or Raney-Nickel in methanol at room temperature at 1 bar.

Compounds of formula V may be prepared from compounds of formula VI,

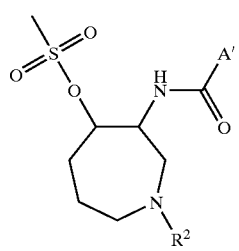

(VI)

wherein A' and $R^2$ are defined hereinabove, by reaction of VI with, for example, sodium azide in DMF at from about 60 to about 90° C.

Compounds of the formula VI may be prepared from compounds of the formula VII,

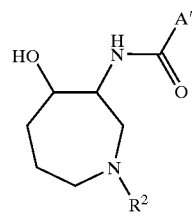

(VII)

wherein A' and $R^2$ are defined hereinabove, by reaction of VII with methylsulfonyl chloride, for example, in pyridine at 0° C.

Compounds of the formula VII are prepared from compounds of the formula VIII and compound IX, wherein A' and $R^2$ are defined hereinabove,

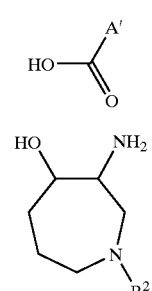

(VIII)

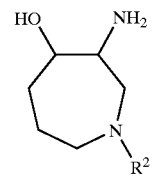

(IX)

This reaction typically involves a two-step one-pot procedure. In the first step, the carboxylate of the compound of formula VIII becomes activated by any of the methods as described for formula III. In the second step, the amine of formula IX is added to the solution in the same way as described for the amine IV.

Compounds of formula VIII are commercially available or synthesized by literature-known procedures and are well known to those skilled in the art.

The synthesis of compound IX is described in EP 0 802 190 A1.

Compounds of formula III are prepared as described in EP 0 663 393 A1 and WO 97/702249.

The invention will now be illustrated in the following non-limiting examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range of from about 18 to about 25° C. and under an atmosphere of an inert gas such as argon or nitrogen;

(iii) column chromatography (by the flash procedure) and high pressure liquid chromatography (HPLC) were performed on Merck Kieselgel silica or Merck Lichroprep RP-18 reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Kofler hot plate apparatus;

(vi) the structures of the end-products of the formula I were confirmed by nuclear (generally proton) magnetic resonance (NMR) and mass spectral techniques (Micromass Platform II machine using APCI or Micromass Platform ZMD using electrospray);
(vii) intermediates were not generally fully characterized and purity was assessed by thin layer chromatography; and
(viii) the following abbreviations were used:
DMF, N,N-dimethylformamide;
DMSO, dimethylsulfoxide;
THF, tetrahydrofuran;
MeOH, methanol;
HCl, hydrochloric acid;
NaH, sodium hydride;
$CH_2Cl_2$, dichloromethane;
$H_2SO_4$, sulfuric acid;
sat., saturated;
sol., solution;
rt, room temperature;
eq, equivalent; and
mp, melting point.

The following examples and references are provided to aid the understanding of the present invention, the true scope of which is set forth in the appended claims. It is understood that modifications can be made in the procedures set forth without departing from the spirit of the invention.

EXAMPLE 1a

N-{(3R, 4R)-4-[4-(2-Fluoro-6-hydroxy-3-methoxy-benzoyl)-benzoylamino]-azepan-3-yl}-isonicotinamide hydrochloride (1a)

0.05 g of 1b were dissolved in 2 mL of a solution of hydrochloric acid in dioxane (4M) at rt and stirred for 24 h. The solvents were evaporated in vacuo and the residue was redissolved in methanol and evaporated to dryness for three times yielding 0.038 g (82%) of 1a as light yellow crystals. MS (ESI): m/z (%): 507 (MH$^+$), 505 ([M−H]$^+$). Mp. 200–222° C.

EXAMPLE 1b (3R,4R)-4-[4-(2-Fluoro-6-methoxymethoxy-3-methoxy-benzoyl)-benzoylamino]-3-[(pyridine-4-carbonyl)-amino]-azepane-1-carboxylic acid tert-butyl ester (1b)

0.167 g of 1c were dissolved in 5 mL $CH_2Cl_2$ at rt. 0.167 g of 4-(2-Fluoro-3-methoxy-6-methoxymethoxy-benzoyl)-benzoic acid (1d), 0.031 g 4-dimethylaminopyridine, and 0.113 g DCC were added. The reaction mixture was stirred for 5 h at rt. The precipitate was filtered off and washed with $CH_2Cl_2$. The residue was evaporated in vacuo to give 0.46 g of crude product. Column chromatography (SiO$_2$, pentane/ethyl acetate 1:10) afforded 0.248 g (76%) of 1b as white crystals. M. p. 106° C.; MS (ESI): m/z (%): 651 (MH$^+$), 649 ([M−H]$^+$).

EXAMPLE 1c (3R,4R)-4-Amino-3-[(pyridine-4-carbonyl)-amino]-azepane-1-carboxylic acid tert-butyl ester (1c)

5.5 g of 1e was dissolved in 135 mL THF and 15 mL ethanol and 1 g Pd/C (10%) was added. The reaction mixture was hydrogenated at 1 bar for 8 h. After filtration, the residue was evaporated in vacuo to give 4.6 g (90%) of 1c as a light brown powder. MS (ESI): m/z (%): 335 (MH$^+$), 333 ([M−H]$^+$).

The synthesis of 1d (4-(2-Fluoro-3-methoxy-6-methoxymethoxy-benzoyl)-benzoic acid) is described in EP 0 663 393 A1.

EXAMPLE 1e (3R,4R)-4-Azido-3-[(pyridine-4-carbonyl)-amino]-azepane-1-carboxylic acid tert-butyl ester (1e)

6.4 g of 1f was dissolved in 150 mL DMF and 5.1 g sodium azide was added. The reaction mixture was stirred for 2 h at 90° C. and then for 24 h at rt. The solvents were evaporated in vacuo and the residue is redissolved in 200 mL ethyl acetate. The organic phase was extracted two times with 200 mL water and once with a saturated solution of NaCl. The organic phase was evaporated in vacuo to give 5.6 g of crude product. Column chromatography (SiO$_2$, hexane/ethyl acetate 3:7) afforded 5.4 g (97%) of 1e as light brown solid. MS (ESI): m/z (%): 361 (MH$^+$), 359 ([M−H]$^+$).

EXAMPLE 1f (3R,4S)-4-Methanesulfonyloxy-3-[(pyridine-4-carbonyl)-amino]-azepane-1-carboxylic acid tert-butyl ester (1f)

6.6 g of 1 g was dissolved in 100 mL pyridine and 6.76 g methanesulfonyl chloride was added at 0° C. The reaction mixture was stirred for 24 h. The solvent was evaporated in vacuo and the residue was redissolved in 100 mL ethyl acetate and extracted three times with water and once with a saturated solution of NaCl. The organic phase was evaporated in vacuo. Column chromatography (SiO$_2$, ethyl acetate/methanol 99:1) gives 6.4 g (79%) of 1f as a white foam. MS (ESI): m/z (%): 414 (MH$^+$), 412 ([M−H]$^+$).

EXAMPLE 1g (3R,4S)-4-Hydroxy-3-[ (pyridine-4-carbonyl)-amino]-azepane-1-carboxylic acid tert-butyl ester (1g)

36.85 g of (3R,4S)-3-Amino-4-hydroxy-azepane-1-carboxylic acid tert-butyl ester, 19.70 g 4-pyridinecarboxylic acid, and 9.76 g dimethylaminopyridine were dissolved in 500 mL $CH_2Cl_2$ and cooled to 5° C. 33.01 g DCC was dissolved in 250 mL $CH_2Cl_2$ and added to the above mixture within 2 h. The reaction mixture was stirred for 48 h at rt. 200 mL water was added and the mixture is stirred for 2 h at rt. The precipitate was filtered off and the organic phase was extracted two times with 500 mL water. The organic solvent was evaporated in vacuo. The crude product was then submitted to column chromatography (SiO$_2$, ethyl acetate/methanol 99:1) to give 46.2 g (86%) of 1 g as a white solid. MS (ESI): m/z (%): 334 (MH$^+$), 336 ([M−H]$^+$).

EXAMPLE 2

In an analogous manner as described in Example 1, the following compounds were obtained and characterized by melting points.
1. N-{(3R,4R)-4-[4-(2-Fluoro-6-hydroxy-3-methyl-benzoyl)-benzoylamino]-azepan-3-yl}-isonicotinamide hydrochloride. Mp. 181–184° C.
2. N-{(3R,4R)-4-[4-(6-Hydroxy-3-methylsulfanyl-benzoyl)-benzoylamino]-azepan-3-yl}-isonicotinamide hydrochloride. Mp. 183–185° C.
3. N-{(3R,4R)-4-[4-(6-Hydroxy-2,3-dihydro-benzo[1,4]dioxine-5-carbonyl)-benzoylamino]-azepan-3-yl}-isonicotinamide hydrochloride. Mp. 230–240° C.

4. N-{(3R,4R)-4-[4-(6-Hydroxy-2,3-dimethoxy-benzoyl)-benzoylamino]-azepan-3-yl}-isonicotinamide hydrochloride. Mp. 185–193° C.

5. N-{(3R,4R)-4-[4-(2-Hydroxy-5-methoxy-benzoyl)-benzoylamino]-azepan-3-yl}-isonicotinamide hydrochloride. Mp. 230–240° C.

6. N-{(3R,4R)-4-[4-(2-Hydroxy-5-methyl-benzoyl)-benzoylamino]-azepan-3-yl}-isonicotinamide hydrochloride. Mp. 215–219° C.

7. N-{(3R,4R)-4-[4-(5-Hydroxy-2-methyl-pyridine-4-carbonyl)-benzoylamino]-azepan-3-yl}-isonicotinamide hydrochloride. Mp. 203–208° C.

8. N-{(3R,4R)-4-[4-(3-Fluoro-5-hydroxy-2-methyl-pyridine-4-carbonyl)-benzoylamino]-azepan-3-yl}-isonicotinamide hydrochloride.

9. N-{(3R,4R)-4-[4-(8-Fluoro-6-hydroxy-quinoline-7-carbonyl)-benzoylamino]-azepan-3-yl}-isonicotinamide hydrochloride. Mp. 247–251° C.

10. N-{(3R,4R)-4-[4-(8-Fluoro-6-hydroxy-2-methyl-quinoline-7-carbonyl)-benzoylamino]-azepan-3-yl}-isonicotinamide hydrochloride. Mp. 255–260° C.

11. N-{(3R,4R)-4-[4-(2-tert-Butyl-8-fluoro-6-hydroxy-quinoline-7-carbonyl)-benzoylamino]-azepan-3-yl}-isonicotinamide hydrochloride. Mp. 215° C.

12. N-{(3R,4R)-4-[4-(6-Hydroxy-quinoline-5-carbonyl)-benzoylamino]-azepan-3-yl}-isonicotinamide hydrochloride. Mp. 215–220° C.

13. N-{(3R,4R)-4-[4-(3-Dimethylamino-2-fluoro-6-hydroxy-benzoyl)-benzoylamino]-azepan-3-yl}-isonicotinamide hydrochloride.

14. N-{(3R,4R)-4-[4-(5-Dimethylamino-2-hydroxy-benzoyl)-benzoylamino]-azepan-3-yl}-isonicotinamide hydrochloride. Mp. 230–245° C.

15. N-{(3R,4R)-4-[4-(2-Hydroxy-5-piperidin-1-yl-benzoyl)-benzoylamino]-azepan-3-yl}-isonicotinamide hydrochloride. Mp. 218–224° C.

16. N-{(3R,4R)-4-[4-(2-Fluoro-6-hydroxy-3-piperidin-1-yl-benzoyl)-benzoylamino]-azepan-3-yl}-isonicotinamide hydrochloride.

17. N-((3R,4R)-4-{4-[3-(3,3-Dimethyl-piperidin-2-yl)-2-fluoro-6-hydroxy-benzoyl]-benzoylamino}-azepan-3-yl)-isonicotinamide hydrochloride. Mp. 265° C.

18. N-((3R,4R)-4-{4-[3-(3,3-Dimethyl-piperidin-2-yl)-6-hydroxy-benzoyl]-benzoylamino}-azepan-3-yl)-isonicotinamide hydrochloride.

19. 2-Amino-N-{(3R,4R)-4-[4-(2-fluoro-6-hydroxy-3-methoxy-benzoyl)-benzoylamino]-azepan-3-yl}-isonicotinamide hydrochloride. Mp. 223–241° C.

20. 2-Amino-N-{(3R,4R)-4-[4-(2-Fluoro-6-hydroxy-3-methyl-benzoyl)-benzoylamino]-azepan-3-yl}-isonicotinamide hydrochloride.

21. 2-Amino-N-{(3R,4R)-4-[4-(6-hydroxy-3-methylsulfanyl-benzoyl)-benzoylamino]-azepan-3-yl}-isonicotinamide hydrochloride.

22. 2-Amino-N-{(3R,4R)-4-[4-(6-Hydroxy-2,3-dihydro-benzo[1,4]dioxine-5-carbonyl)-benzoylamino]-azepan-3-yl}-isonicotinamide hydrochloride.

23. 2-Amino-N-{(3R,4R)-4-[4-(6-Hydroxy-2,3-dimethoxy-benzoyl)-benzoylamino]-azepan-3-yl}-isonicotinamide hydrochloride.

24. 2-Amino-N-{(3R,4R)-4-[4-(2-Hydroxy-5-methoxy-benzoyl)-benzoylamino]-azepan-3-yl}-isonicotinamide hydrochloride.

25. 2-Amino-N-{(3R,4R)-4-[4-(2-Hydroxy-5-methyl-benzoyl)-benzoylamino]-azepan-3-yl}-isonicotinamide hydrochloride.

26. 2-Amino-N-{(3R,4R)-4-[4-(5-Hydroxy-2-methyl-pyridine-4-carbonyl)-benzoylamino]-azepan-3-yl}-isonicotinamide hydrochloride.

27. 2-Amino-N-{(3R,4R)-4-[4-(3-Fluoro-5-hydroxy-2-methyl-pyridine-4-carbonyl)-benzoylamino]-azepan-3-yl}-isonicotinamide hydrochloride.

28. 2-Amino-N-{(3R,4R)-4-[4-(8-Fluoro-6-hydroxy-quinoline-7-carbonyl)-benzoylamino]-azepan-3-yl}-isonicotinamide hydrochloride.

29. 2-Amino-N-{(3R,4R)-4-[4-(8-Fluoro-6-hydroxy-2-methyl-quinoline-7-carbonyl)-benzoylamino]-azepan-3-yl}-isonicotinamide hydrochloride.

30. 2-Amino-N-{(3R,4R)-4-[4-(2-tert-Butyl-8-fluoro-6-hydroxy-quinoline-7-carbonyl)-benzoylamino]-azepan-3-yl}-isonicotinamide hydrochloride.

31. 2-Amino-N-{(3R,4R)-4-[4-(6-Hydroxy-quinoline-5-carbonyl)-benzoylamino]-azepan-3-yl}-isonicotinamide hydrochloride.

32. 2-Amino-N-{(3R,4R)-4-[4-(3-Dimethylamino-2-fluoro-6-hydroxy-benzoyl)-benzoylamino]-azepan-3-yl}-isonicotinamide hydrochloride.

33. 2-Amino-N-{(3R,4R)-4-[4-(5-Dimethylamino-2-hydroxy-benzoyl)-benzoylamino]-azepan-3-yl}-isonicotinamide hydrochloride.

34. 2-Amino-N-{(3R,4R)-4-[4-(2-Hydroxy-5-piperidin-1-yl-benzoyl)-benzoylamino]-azepan-3-yl}-isonicotinamide hydrochloride.

35. 2-Amino-N-{(3R,4R)-4-[4-(2-Fluoro-6-hydroxy-3-piperidin-1-yl-benzoyl)-benzoylamino]-azepan-3-yl}-isonicotinamide hydrochloride.

36. 2-Amino-N-((3R,4R)-4-{4-[3-(3,3-Dimethyl-piperidin-2-yl)-2-fluoro-6-hydroxy-benzoyl]-benzoylamino}-azepan-3-yl)-isonicotinamide hydrochloride.

37. 2-Amino-N-((3R,4R)-4-{4-[3-(3,3-Dimethyl-piperidin-2-yl)-6-hydroxy-benzoyl]-benzoylamino}-azepan-3-yl)-isonicotinamide hydrochloride.

38. Pyrimidine-4-carboxylic acid {(3R,4R)-4-[4-(2-fluoro-6-hydroxy-3-methoxy-benzoyl)-benzoylamino]-azepan-3-yl}-amide hydrochloride. Mp. 256–265° C.

39. Pyrimidine-4-carboxylic acid {(3R,4R)-4-[4-(2-Fluoro-6-hydroxy-3-methyl-benzoyl)-benzoylamino]-azepan-3-yl}-amide hydrochloride.

40. Pyrimidine-4-carboxylic acid {(3R,4R)-4-[4-(6-hydroxy-3-methylsulfanyl-benzoyl)-benzoylamino]-azepan-3-yl}-amide hydrochloride.

41. Pyrimidine-4-carboxylic acid {(3R,4R)-4-[4-(6-Hydroxy-2,3-dihydro-benzo[1,4]dioxine-5-carbonyl)-benzoylamino]-azepan-3-yl}-amide hydrochloride.

42. Pyrimidine-4-carboxylic acid {(3R,4R)-4-[4-(6-Hydroxy-2,3-dimethoxy-benzoyl)-benzoylamino]-azepan-3-yl}-amide hydrochloride.

43. Pyrimidine-4-carboxylic acid {(3R,4R)-4-[4-(2-Hydroxy-5-methoxy-benzoyl)-benzoylamino]-azepan-3-yl}-amide hydrochloride.

44. Pyrimidine-4-carboxylic acid {(3R,4R)-4-[4-(2-Hydroxy-5-methyl-benzoyl)-benzoylamino]-azepan-3-yl}-amide hydrochloride.

45. Pyrimidine-4-carboxylic acid {(3R,4R)-4-[4-(5-Hydroxy-2-methyl-pyridine-4-carbonyl)-benzoylamino]-azepan-3-yl}-amide hydrochloride.

46. Pyrimidine-4-carboxylic acid {(3R,4R)-4-[4-(3-Fluoro-5-hydroxy-2-methyl-pyridine-4-carbonyl)-benzoylamino]-azepan-3-yl}-amide hydrochloride.
47. Pyrimidine-4-carboxylic acid {(3R,4R)-4-[4-(8-Fluoro-6-hydroxy-quinoline-7-carbonyl)-benzoylamino]-azepan-3-yl}-amide hydrochloride.
48. Pyrimidine-4-carboxylic acid {(3R,4R)-4-[4-(8-Fluoro-6-hydroxy-2-methyl-quinoline-7-carbonyl)-benzoylamino]-azepan-3-yl}-amide hydrochloride.
49. Pyrimidine-4-carboxylic acid {(3R,4R)-4-[4-(2-tert-Butyl-8-fluoro-6-hydroxy-quinoline-7-carbonyl)-benzoylamino]-azepan-3-yl}-amide hydrochloride.
50. Pyrimidine-4-carboxylic acid {(3R,4R)-4-[4-(6-Hydroxy-quinoline-5-carbonyl)-benzoylamino]-azepan-3-yl}-amide hydrochloride.
51. Pyrimidine-4-carboxylic acid {(3R,4R)-4-[4-(3-Dimethylamino-2-fluoro-6-hydroxy-benzoyl)-benzoylamino]-azepan-3-yl}-amide hydrochloride.
52. Pyrimidine-4-carboxylic acid {(3R,4R)-4-[4-(5-Dimethylamino-2-hydroxy-benzoyl)-benzoylamino]-azepan-3-yl}-amide hydrochloride.
53. Pyrimidine-4-carboxylic acid {(3R,4R)-4-[4-(2-Hydroxy-5-piperidin-1-yl-benzoyl)-benzoylamino]-azepan-3-yl}-amide hydrochloride.
54. Pyrimidine-4-carboxylic acid {(3R,4R)-4-[4-(2-Fluoro-6-hydroxy-3-piperidin-1-yl-benzoyl)-benzoylamino]-azepan-3-yl}-amide hydrochloride.
55. Pyrimidine-4-carboxylic acid ((3R,4R)-4-{4-[3-(3,3-Dimethyl-piperidin-2-yl)-2-fluoro-6-hydroxy-benzoyl]-benzoylamino}-azepan-3-yl)-amide hydrochloride.
56. Pyrimidine-4-carboxylic acid ((3R,4R)-4-{4-[3-(3,3-Dimethyl-piperidin-2-yl)-6-hydroxy-benzoyl]-benzoylamino}-azepan-3-yl)-amide hydrochloride.
57. N-{(3R,4R)-4-[4-(3-Methyl-benzoyl)-benzoylamino]-azepan-3-yl}-isonicotinamide hydrochloride. Mp. 190–196° C.
58. N-{(3R,4R)-4-[4-(2,5-Dihydroxy-benzoyl)-benzoylamino]-azepan-3-yl}-isonicotinamide hydrochloride. Mp. 108–114° C.
59. N-{(3R,4R)-4-[4-(2-Hydroxy-5-isopropoxy-benzoyl)-benzoylamino]-azepan-3-yl}-isonicotinamide hydrochloride. Mp. 243–249° C.
60. N-{(3R,4R)-4-[4-(3-Aminomethyl-6-hydroxy-benzoyl)-benzoylamino]-azepan-3-yl}-isonicotinamide hydrochloride. Mp. 215–218° C.
61. N-{(3R,4R)-4-[4-(3-<1-Amino-cyclopropyl>-6-hydroxy-benzoyl)-benzoylamino]-azepan-3-yl}-isonicotinamide hydrochloride.
62. N-((3R,4R)-4-{4-[2-Hydroxy-5-(piperidin-2-yl)-benzoyl]-benzoylamino}-azepan-3-yl)-isonicotinamide hydrochloride. Mp. 195–210° C.
63. N-((3R,4R)-4-{4-[3-(3,3-Dimethyl-piperidin-1-yl)-6-hydroxy-benzoyl]-benzoylamino}-azepan-3-yl)-isonicotinamide hydrochloride. Mp. 194–198° C.
64. N-((3R,4R)-4-{4-[3-(3,3-Dimethyl-piperidin-1-yl)-2-fluoro-6-hydroxy-benzoyl]-benzoylamino}-azepan-3-yl)-isonicotinamide hydrochloride.
65. N-((3R,4R)-4-{4-[3-(4,4-Dimethyl-piperidin-1-yl)-6-hydroxy-benzoyl]-benzoylamino}-azepan-3-yl)-isonicotinamide hydrochloride. Mp. 229–234° C.
66. N-{(3R,4R)-4-[4-(2-Hydroxy-5-isopropylamino-benzoyl)-benzoylamino]-azepan-3-yl}-isonicotinamide hydrochloride. Mp. 227–230° C.
67. N-{(3R,4R)-4-[4-(2-Hydroxy-5-<2-methyl-propylamino>-benzoyl)-benzoylamino]-azepan-3-yl}-isonicotinamide hydrochloride. Mp. 223–226° C.
68. N-{(3R,4R)-4-[4-(3-<2,2-Dimethyl-propylamino>-6-hydroxy-benzoyl)-benzoylamino]-azepan-3-yl}-isonicotinamide hydrochloride. Mp. 243–246° C.
69. N-{(3R,4R)-4-[4-(2,5-Dimethoxy-6-fluoro-benzoyl)-benzoylamino]-azepan-3-yl}-isonicotinamide hydrochloride
70. N-{(3R,4R)-4-[4-(3-<3-Azabicyclo[3.2.1]oct-3-yl>-6-hydoxy-benzoyl)-benzoylamino]-azepan-3-yl}-isonicotinamide hydrochloride.
71. 4-Hydroxybenzoic acid {(3R,4R)-4-[4-(2-Fluoro-6-hydroxy-3-methoxy-benzoyl)-benzoylamino]-azepan-3-yl}-amide hydrochloride. Mp. 190–196° C.
72. 4-Hydroxybenzoic acid {(3R,4R)-4-[4-(3-Dimethylamino-6-hydroxy-benzoyl)-benzoylamino]-azepan-3-yl}-amide hydrochloride. Mp. 203–206° C.
73. 3,5-Dimethyl-4-hydroxybenzoic acid {(3R,4R)-4-[4-(2-Fluoro-6-hydroxy-3-methoxy-benzoyl)-benzoylamino]-azepan-3-yl}-amide hydrochloride. Mp. 180–183° C.
74. 3,5-Dimethyl-4-hydroxybenzoic acid {(3R,4R)-4-[4-(3-Dimethylamino-6-hydroxy-benzoyl)-benzoylamino]-azepan-3-yl}-amide hydrochloride. Mp. 217–219° C.

EXAMPLE 3

In order to study AKT inhibitory activity of the compounds according to the invention, an ELISA-based assay was developed for AKT. The assay design utilized a N-terminally biotinylated substrate peptide. When this substrate was phosphorylated by the AKT kinase, the product was recognized by a substrate/sequence-specific antibody known to bind to particular phosphorylated serine residues. For this assay, a Biotin-SGRARTSSFAEPG peptide and anti-phospho-GSK-3α Ser21 antibody (rabbit) from Cell Signaling Technology/New England Biolabs were used.

The enzymatic reactions were carried out with AKT expressed in Sf9 cells (100 ng/reaction), substrate peptide (300 nM) and ATP (5 $\mu$M) in the absence or presence of different concentrations of compounds dissolved in DMSO. The final concentration of DMSO was 1%. The mixtures were reacted for 30 min at room temperature in assay buffer containing 50 mM Tris-HCl, 10 mM $MgCl_2$, 1.0 mM DTT, 2 mM $Na_3VO_4$, pH 7.5, in a final volume of 40 $\mu$l. The reaction was stopped with addition of 10 $\mu$l 0,12 M EDTA/ 0,12 M EGTA. The reaction mixture was transferred to a SA-coated micro-titer-plate. After 1 h incubation, the plate was washed with PBS using a 384-well Embla plate washer. Anti-phospho-GSK-3α Ser21 antibody was added. After 1 h incubation the plate was washed with PBS and bound antibody was detected by addition of polyclonal<Rabbit>S-IgG-POD-conjugate from Roche Diagnostics GmbH. After 1 h incubation, the plate was washed with PBS. Amount of phosphorylated peptide was measured by an enzyme-catalyzed color reaction (ABTS conversion) and photometrical measurement at 405 nm.

To determine $IC_{50}$ values the compounds were tested in the concentration range from 250 nM to 10 pM. Calculation of $IC_{50}$ values were performed with ActivityBase. The compounds according to the invention gave $IC_{50}$ values in the range of from about 3 to about 116 nM, as shown in the following but non limiting Examples 1a, 2-1, 2-2, 2-4, 2-5, 2-6 values of 3, 7, 11, 116, 15 and 16 nM were determined respectively.

EXAMPLE 4

Additionally to Example 3 the acticity of compounds according to the invention was studied on a cellular AKT activity assay as follows:

Prostate cancer cell line LNCaP was passaged in RPMI 1640 with 10% fetal calf serum, 50 units/ml penicillin, and 50 units/ml streptomycin. LNCaP cells were characterized by a constitutive activation of AKT. Constitutive active AKT phosphorylates glycogen synthase kinase-3 (GSK-3) at Ser21/Ser9 in LNCaP cells. To measure the effect of compounds on the activity of AKT in living cells, LNCaP cells were treated with various concentrations of inhibitors (6 μM to 187 nM). After 1 h, the cells were were harvested in lysis solution containing 50 mM HEPES (pH 7.0), 150 mM NaCl, 1.5 mM MgCl2 ,1 mM EGTA, 100 mM NaF, 10 mM sodium PPi, 10% glycerol, 1% Triton X-100, 1 mM Na3 VO4,10 mM pepstatin, 10 mg/ml aprotinin, 5 mM iodoacetic acid, and 2 mg/ml leupeptin. The proteins from whole cell extracts were electrophoresed on 7.5% SDS/PAGE gels. Afterwards, proteins were transferred onto Nitrocellulose filter and immunoblotting using the enhanced chemiluminescence (ECL) detection system (Amersham Pharmacia) was performed. The level of GSK-3-Ser21/Ser9 phosphorylation was thereby determined using polyclonal anti-P-GSK-3-Ser-21/9 antibody (rabbit; New England Biolabs). Here, for the above-mentioned, but non limiting Examples 1a, 2-1, 2-2, 2-4, 2-5, 2-6, values of 3, 3, 1.5,>24, 2 and 1 μM were found respectively.

EXAMPLE 5

In order to prove the increased plasma-stability of the compounds according to this invention, mouse plasma tests were used as follows:

Samples of mouse plasma containing each a compound according to the invention in a standard concentration (10 μmol/1) were prepared. After defined periods of time with respect to the addition of said compounds to the mouse-plasma (t=0, 0.5, 1, 2, 4 h ), equal portions were isolated from the plasma, separated with HPLC and analyzed by mass spectrometry. During all these steps, the temperature was kept constant at 37° C.

In the following table, the plasma stability of compounds according to the invention was compared to one of the selected compounds from EP 0 663 393 A1.

TABLE 1

| Reference-Compound from EP 0 663 393 A1 | Decrease [%] |
| --- | --- |
| Example 46 | 100 (after 2 h) |
| Compounds according to the invention | Decrease [%] (after 4 h) |
| Example 1a | 6.2 |
| Example 2-1 | 21.9 |
| Example 2-2 | 26.9 |

EXAMPLE 6

| Tablet formulation | | |
| --- | --- | --- |
| Item | Ingredients | mg/Tablet |
| 1 | Compound 2-1 | 25 | 100 |
| 2 | Anhydrous Lactose | 73 | 35 |
| 3 | Croscarmellose sodium | 6 | 8 |

-continued

| Tablet formulation | | |
| --- | --- | --- |
| Item | Ingredients | mg/Tablet |
| 4 | Povidone K30 | 5 | 6 |
| 5 | Magnesium Stearate | 1 | |
| | Total Weight | 110 | 150 |

Compound 2-1 is described in Example 2.
Procedure:
Mix Items 1, 2 and 3 in a suitable mixer for 15 minutes.
Granulate the powder mix from Step 1 with 20% Povidone K30 Solution (Item 4).
Dry the granulation from Step 2 at 50° C.
Pass the granulation from Step 3 through a suitable milling equipment.
Add the Item 5 to the milled granulation Step 4 and mix for 3 minutes.
Compress the granulation from Step 5 on a suitable press.

EXAMPLE 7

| Capsule formulation | | |
| --- | --- | --- |
| Item | Ingredients | mg/Capsule |
| 1 | Compound 2-1 | 50 | 100 |
| 2 | Anhydrous Lactose | 123 | 148 |
| 3 | Corn Starch | 35 | 40 |
| 4 | Talc | 15 | 10 |
| 5 | Magnesium Stearate | 2 | 2 |
| | Total Fill Weight | 225 | 300 |

Compound 2-1 is described in Example 2.
Manufacturing Procedure:
Mix Items 1, 2 and 3 in a suitable mixer for 15 minutes.
Add Items 4 & 5 and mix for 3 minutes.
Fill into a suitable capsule.
What is claimed is:
1. A compound of formula (I)

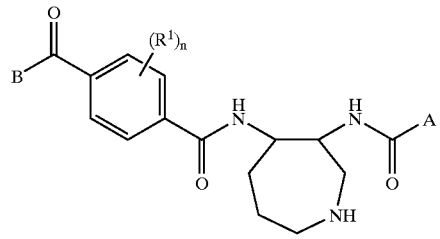

wherein
A is a non-aromatic, 3 to 7 carbon atom, mono-or bicyclic carbocyclic group or a non-aromatic, 3 to 7 membered, mono- or bicyclic heterocyclic group having one or two heteroatoms chosen from nitrogen, oxygen or sulfur, said groups being substituted by 1, 2, or 3 substituents selected from halogen, alkyl, trifluoromethyl, hydroxy, alkoxy, aryl, hetaryl, arylalkyl, arylalkyloxy, aryloxy, alkylenedioxy, nitro, amino, alkylamino, dialkylamino, alkanoylamino or acyl or unsubstituted and optionally annulated by an aryl or hetaryl group or A is an aryl or hetaryl group said hetaryl groups having one or two hetero atoms chosen from nitrogen, oxygen or sulfur;

B is a phenyl ring which may be unsubstituted or substituted by 1, 2 or 3 substituents independently selected from a halogen atom, an (1–4C)alkyl, trifluoromethyl, hydroxy, (1–4C)alkoxy, nitro, amino, amino(1–4C)alkyl, (1–4C)alkylamino, di[(1–4C)alkyl]amino, (1–4C)alkanoylamino, (1–4C)alkylthio, (1–4C)alkoxycarbonyl, a (1–3C)alkylenedioxy, an acyl selected from formyl, acetyl, propionyl, benzoyl or phenylacetyl, a non-aromatic, 3 to 7 carbon atom, mono- or bicyclic carbocyclic group or a non-aromatic, 3 to 7 membered, mono- or bicyclic heterocyclic group having one or two heteroatoms, said groups being substituted or unsubstituted and optionally annulated by a non-aromatic, 3 to 7 carbon atom, mono- or bicyclic, substituted or unsubstituted carbocyclic group or by a non-aromatic, 3 to 7 membered, mono- or bicyclic, substituted or unsubstituted heterocyclic group having one or two heteroatoms, or a non-aromatic, 3 to 7 membered, mono- or bicyclic, substituted or unsubstituted heterocyclic group having one or two heteroatoms, $(R^1)_n$ is the same or different halogen atom, a (1–4C) alkyl-, or a (1–4C)alkoxy-group, and n=0–4;

its stereoisomers, enantiomers or racemates;

or a pharmaceutically acceptable salt thereof.

2. The compound of formula (I) according to claim 1, wherein

B is a phenyl ring which may be unsubstituted or substituted by 1, 2 or 3 substituents independently selected from a halogen atom, an (1–4C)alkyl, trifluoromethyl, hydroxy, (1–4C)alkoxy, nitro, amino, (1–4C)alkylamino, di[(1–4C)alkyl]amino, (1–4C)alkanoylamino, (1–4C)alkylthio, (1–4C)alkoxycarbonyl, a (1–3C)alkylenedioxy, an acyl selected from formyl, acetyl, propionyl, benzoyl or phenylacetyl, a non-aromatic, 3 to 7 carbon atom, mono- or bicyclic carbocyclic group or a non-aromatic, 3 to 7 membered, mono- or bicyclic heterocyclic group having one or two heteroatoms, said groups being substituted or unsubstituted and which may be annulated by a non-aromatic, 3 to 7 carbon atom, mono- or bicyclic, substituted or unsubstituted carbocyclic group or by a non-aromatic, 3 to 7 membered, mono- or bicyclic, substituted or unsubstituted heterocyclic group having one or two heteroatoms, or a non-aromatic, 3 to 7 membered, mono- or bicyclic, substituted or unsubstituted heterocyclic group having one or two heteroatoms, $(R^1)_n$ is the same or different halogen atom, a (1–4C) alkyl-, or a (1–4C)alkoxy-group, and n=0–4;

its stereoisomers, enantiomers or racemates;

or a pharmaceutically acceptable salt thereof.

3. The compound of formula (I) according to claim 1, wherein

A is pyridine, 2-aminopyridine or pyrimidine;

B is a substituent, chosen from 2-fluoro-6-hydroxy-3-methoxy-phenyl, 2-fluoro-6-hydroxy-3-methyl-phenyl, 6-hydroxy-3-methylsulfanyl-phenyl, 6-hydroxy-2,3-dihydro-benzo[1,4]dioxine-5-yl, 6-hydroxy-2,3-dimethoxy-phenyl, 2-hydroxy-5-methoxy-phenyl, 2-hydroxy-5-methyl-phenyl, 5-hydroxy-2-methyl-pyridine-4-yl, 3-fluoro-5-hydroxy-2-methyl-pyridine-4-yl, 8-fluoro-6-hydroxy-quinoline-7-yl, 8-fluoro-6-hydroxy-2-methyl-quinoline-7-yl, 2-tert-butyl-8-fluoro-6-hydroxy-quinoline-7-yl, 6-hydroxy-quinoline-5-yl, 3-dimethylamino-2-fluoro-6-hydroxy-phenyl, 5-dimethylamino-2-hydroxy-phenyl, 2-hydroxy-5-piperidin-1-yl-phenyl, 2-fluoro-6-hydroxy-3-piperidin-1-yl-phenyl, 3-(3,3-dimethyl-piperidin-2-yl)-2-fluoro-6-hydroxy-phenyl, or 3-(3,3-dimethyl-piperidin-2-yl)-6-hydroxy-phenyl;

$(R^1)_n$ is the same or different halogen atom, a (1–4C) alkyl-, or a (1–4C)alkoxy-group, and n=0.

4. The compound of formula (I) according to claim 1 wherein the compound is an optical isomer of the compound of formula (I).

5. A compound of formula (IV)

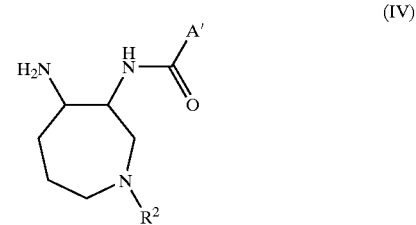

(IV)

wherein A' is a non-aromatic, 3 to 7 carbon atom, mono- or bicyclic, substituted or unsubstituted carbocyclic group or a non-aromatic, 3 to 7 membered, mono- or bicyclic, substituted or unsubstituted heterocyclic group having one or two heteroatoms or A' is an aryl or hetaryl group having one or two hetero atoms selected from nitrogen, oxygen or sulfur and $R^2$ is a protecting group selected from t-butoxycarbonyl or methoxymethyl, or a pharmaceutically acceptable salt thereof.

6. The compound of claim 5 wherein the compound is an optical isomer thereof.

7. A compound of formula (V)

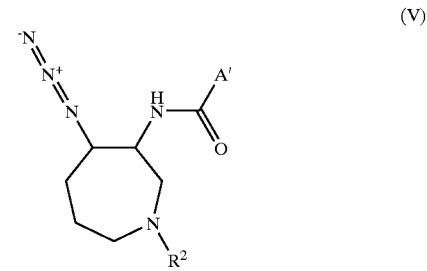

(V)

wherein A' is a non-aromatic, 3 to 7 carbon atom, mono- or bicyclic, substituted or unsubstituted carbocyclic group or a non-aromatic, 3 to 7 membered, mono- or bicyclic, substituted or unsubstituted heterocyclic group having one or two heteroatoms or A' is an aryl or hetaryl group having one or two hetero atoms selected from nitrogen, oxygen or sulfur and $R^2$ is a protecting group selected from t-butoxycarbonyl or methoxymethyl, or a pharmaceutically acceptable salt thereof.

8. The compound of claim 7 wherein the compound is an optical isomer thereof.

9. A compound of formula (VI)

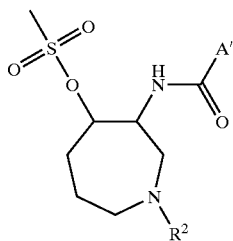

(VI)

wherein A' is a non-aromatic, 3 to 7 carbon atom, mono-or bicyclic, substituted or unsubstituted carbocyclic group or a non-aromatic, 3 to 7 membered, mono- or bicyclic, substituted or unsubstituted heterocyclic group having one or two heteroatoms or A' is an aryl or hetaryl group having one or two hetero atoms selected from nitrogen, oxygen or sulfur and $R^2$ is a protecting group selected from t-butoxycarbonyl or methoxymethyl, or a pharmaceutically acceptable salt thereof.

10. The compound of claim 9 wherein the compound is an optical isomer thereof.

11. A process for the manufacture of the compounds as claimed in claim 1, which comprises cleaving off the protecting group $R^2$ from a compound of the formula

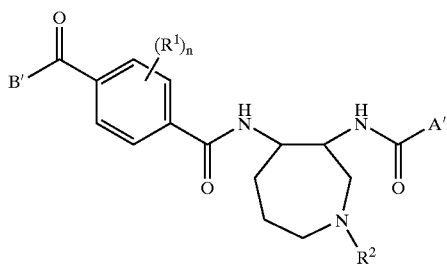

(II)

wherein A' is a non-aromatic, 3 to 7 carbon atom, mono- or bicyclic, substituted or unsubstituted carbocyclic group or a non-aromatic, 3 to 7 membered, mono- or bicyclic, substituted or unsubstituted heterocyclic group having one or two heteroatoms or A' is an aryl or hetaryl group having one or two hetero atoms selected from nitrogen, oxygen or sulfur or a suitably protected derivative thereof, B' is a phenyl ring which may be unsubstituted or substituted by 1, 2 or 3 substituents independently selected from a halogen atom, an (1–4C)alkyl, trifluoromethyl, hydroxy, (1–4C)alkoxy, nitro, amino, amino(1–4C) alkyl, (1–4C)alkylamino, di[(1–4C)alkyl]amino, (1–4C)alkanoylamino, (1–4C)alkylthio, (1–4C) alkoxycarbonyl, a (1–3C)alkylenedioxy, an acyl, a non-aromatic, 3 to 7 carbon atom, mono- or bicyclic, substituted or unsubstituted carbocyclic group or a non-aromatic, 3 to 7 membered, mono- or bicyclic, substituted or unsubstituted heterocyclic group having one or two heteroatoms, and which may be annulated by a non- aromatic, 3 to 7 carbon atom, mono- or bicyclic, substituted or unsubstituted carbocyclic group or by a non-aromatic, 3 to 7 membered, mono- or bicyclic, substituted or unsubstituted heterocyclic group having one or two heteroatoms, a non-aromatic, 3 to 7 membered, mono- or bicyclic, substituted or unsubstituted heterocyclic group having one or two heteroatoms or a protected derivative thereof, $(R^1)_n$ is the same or different halogen atom, a (1–4C)alkyl-, or a (1–4C)alkoxy- group; $R^2$ is a protecting group, and n=0–4.

12. The process of claim 11 which further comprises protecting the groups present in A' and B'.

13. The process of claim 11 which further comprises converting the compound into its pharmaceutically acceptable salt.

14. The process according to claim 11, wherein compounds of the formula (II) are obtained by using compounds of formulas (IV), (V) and (VI) as intermediates.

15. A pharmaceutical composition containing a compound of formula (I) or a pharmaceutically acceptable salt thereof as claimed in claim 1 and a pharmaceutically acceptable adjuvant.

* * * * *